US010876679B2

(12) United States Patent
Monir (10) Patent No.: US 10,876,679 B2
(45) Date of Patent: Dec. 29, 2020

(54) PERSONAL RADIATION GARMENT SUSPENSION SYSTEM

(71) Applicant: George Monir, Maitland, FL (US)

(72) Inventor: George Monir, Maitland, FL (US)

( * ) Notice: Subject to any disclaimer, the term of this patent is extended or adjusted under 35 U.S.C. 154(b) by 16 days.

(21) Appl. No.: 16/001,250

(22) Filed: Jun. 6, 2018

(65) Prior Publication Data

US 2019/0234554 A1  Aug. 1, 2019

Related U.S. Application Data

(60) Provisional application No. 62/623,237, filed on Jan. 29, 2018.

(51) Int. Cl.
| | |
|---|---|
| *F16M 11/18* | (2006.01) |
| *F16M 13/04* | (2006.01) |
| *F16M 13/02* | (2006.01) |
| *G21F 3/02* | (2006.01) |
| *F16M 11/20* | (2006.01) |
| *F16M 11/10* | (2006.01) |

(52) U.S. Cl.
CPC .......... *F16M 11/18* (2013.01); *F16M 13/027* (2013.01); *F16M 13/04* (2013.01); *F16M 11/10* (2013.01); *F16M 11/2064* (2013.01); *F16M 11/2092* (2013.01); *G21F 3/02* (2013.01)

(58) Field of Classification Search
CPC ... G21F 3/02; G21F 3/03; F21V 21/36; A61B 6/107; F16M 11/00; F16M 11/18; F16M 11/2064; F16M 11/2092; F16M 13/027
See application file for complete search history.

(56) References Cited

U.S. PATENT DOCUMENTS

| | | | | |
|---|---|---|---|---|
| 466,509 A | * | 1/1892 | Painter | H01H 17/00 200/544 |
| 4,254,341 A | * | 3/1981 | Herr | A61B 6/107 250/519.1 |
| 4,256,098 A | * | 3/1981 | Swan | A62B 35/0093 128/845 |
| 4,489,308 A | * | 12/1984 | Logan, Jr. | G08B 17/00 191/12.2 A |

(Continued)

FOREIGN PATENT DOCUMENTS

| | | | |
|---|---|---|---|
| DE | 2934955 A1 | * 3/1981 | ............. A61B 6/447 |
| DE | 202018103817 | * 10/2018 | |
| KR | 1020160045423 | * 9/2016 | |

OTHER PUBLICATIONS

Chicago Pneumatic, Operator's Manual, 2010 (Year: 2010).*

(Continued)

*Primary Examiner* — Eret C McNichols
(74) *Attorney, Agent, or Firm* — Jason T. Daniel, Esq.; Daniel Law Offices, P.A.

(57) ABSTRACT

A suspension system for a personal radiation garment includes a ceiling mount having a flanged drop tube extending vertically, and at least one extension arm that rotates horizontally via bearing joints. A suspension assembly having at least one hoist is positioned along the distal end of the outermost extension arm, and a garment coupler is connected to a cable extending from the hoist. Each of the one or more hoists include an adjustable tensioning mechanism that is controlled manually or by a motor having a controller and a switch.

15 Claims, 10 Drawing Sheets

(56) References Cited

U.S. PATENT DOCUMENTS

| | | | | |
|---|---|---|---|---|
| 5,519,597 A * | 5/1996 | Tsai | ........................ | F21V 21/38 248/328 |
| 5,704,881 A * | 1/1998 | Dudley | .............. | A63B 69/0064 482/43 |
| 6,080,087 A * | 6/2000 | Bingham | .............. | A47D 13/046 482/69 |
| 6,142,439 A * | 11/2000 | Aramaki | .................. | B66D 1/60 248/327 |
| 6,331,121 B1 * | 12/2001 | Raeford, Sr. | .......... | H01R 13/72 174/67 |
| 6,431,515 B1 | 8/2002 | Gampe et al. | | |
| 6,464,190 B1 * | 10/2002 | Aramaki | ................. | F21V 21/38 248/327 |
| 6,464,208 B1 * | 10/2002 | Smith | .................... | A61H 3/008 212/97 |
| 6,523,195 B1 * | 2/2003 | Rodier | ................. | A61G 7/1015 104/89 |
| 7,883,450 B2 * | 2/2011 | Hidler | .................... | A61H 3/008 212/104 |
| 8,651,343 B2 * | 2/2014 | Huang | ................... | A47G 25/90 223/85 |
| 9,349,492 B1 | 5/2016 | Ganus | | |
| 9,629,769 B2 * | 4/2017 | Newkirk | ................... | A61G 7/10 |
| 10,020,083 B1 * | 7/2018 | Heesch | .............. | A41D 13/1209 |
| 10,478,371 B2 * | 11/2019 | Stockmaster | .......... | G16H 40/63 |
| 2005/0115914 A1 * | 6/2005 | Chepurny | .............. | A61G 7/1015 212/328 |
| 2007/0004567 A1 * | 1/2007 | Shetty | .................... | A61H 3/008 482/69 |
| 2007/0138415 A1 | 6/2007 | Rees | | |
| 2009/0184269 A1 * | 7/2009 | Rees | ...................... | A61B 6/107 250/516.1 |
| 2009/0256044 A1 * | 10/2009 | Miller | ....................... | G21F 3/02 248/317 |
| 2010/0000002 A1 | 1/2010 | Rees | | |
| 2010/0107320 A1 * | 5/2010 | Rees | ...................... | A61B 6/107 2/456 |
| 2011/0174997 A1 * | 7/2011 | Rees | ...................... | A61B 6/107 250/516.1 |
| 2012/0280004 A1 | 11/2012 | Huang | | |
| 2013/0306824 A1 * | 11/2013 | Miller | ................ | A41D 13/0002 248/342 |
| 2016/0058078 A1 * | 3/2016 | Monir | .................... | G21F 3/025 248/317 |
| 2017/0009937 A1 * | 1/2017 | Shin | ..................... | F16M 13/027 |
| 2017/0326013 A1 | 11/2017 | Hyde et al. | | |
| 2018/0117733 A1 * | 5/2018 | Steinle | ................... | F16F 1/128 |

OTHER PUBLICATIONS

Ingersoll Rand, Ergonomic Handling Systems, 2013, pp. 20-31 (Year: 2013).*

"Weightless Lead"; www.weightlesslead.com/; Accessed from Internet Feb. 21, 2019 (6 pages).

\* cited by examiner

PERSONAL RADIATION GARMENT SUSPENSION SYSTEM

CROSS-REFERENCE TO RELATED APPLICATIONS

This application claims the benefit of U.S. Application Ser. No. 62/623,237 filed on Jan. 29, 2018, the contents of which are incorporated herein by reference.

TECHNICAL FIELD

The present invention relates generally to radiation protective systems, and more particularly to an overhead suspension system for connecting to a radiation protective garment.

BACKGROUND

The statements in this section merely provide background information related to the present disclosure and may not constitute prior art.

Medical professionals such as doctors and nurses routinely wear radiation protective garments while performing medical procedures such as cardiac catheterizations, for example. These garments are typically constructed as vests or aprons, which include radiation-absorbing materials such as lead or other metals, for example.

Although useful for preventing unwanted radiation exposure, these garments are often uncomfortable, ill-fitting and heavy, thereby placing a significant stress on the users' back and shoulders. Moreover, unlike patients who wear these garments for short periods of time, medical professionals must often wear these garments for several hours each day, thereby increasing the toll on their bodies over time.

Previous attempts have been made to create a system that provides a suspended radiation garment for use by medical professionals. Although useful in concept, such systems typically suffer from multiple drawbacks. For example, these systems utilize a proprietary radiation protective garment that is permanently secured to the overhead system thus making these garments difficult to clean and preventing medical professionals from utilizing their personal (and often custom made) radiation garments.

Additionally, such systems utilize a series of exposed overhead channels on which a guide is pulled as the user moves. Owing to this arrangement, such systems require the user to make exaggerated movements to account for the weight and movement of the suit, and often results in dust (which accumulates along the length of the channels) falling into the otherwise sterile environment. For each of these reasons, such systems have met with extremely limited commercial success.

Accordingly, the need exists for a personal radiation garment suspension system that can be utilized with any type of protective garment in a sterile environment that does not suffer from the drawbacks outlined above.

SUMMARY OF THE INVENTION

The present invention is directed to suspension system for a personal radiation garment. One embodiment of the present invention can include a ceiling mount having a flanged drop tube that extends vertically downward from the ceiling mount. One or more extension arms can be connected to the end of the drop tube via a joint, and can rotate 360 degrees horizontally. Subsequent extension arms are connected by stacked joints and can rotate 360 degrees relative to each other.

In one embodiment, a suspension assembly can be positioned along the distal end of the outermost extension arm. One or more hoists can be positioned within the housing and can include an adjustable tensioning mechanism and one or more cables that extend downward therefrom. Each of the cables can be in communication with a garment coupler that has connectors for engaging complementary connectors of a personal radiation garment.

In one embodiment, each of the one or more hoists can include an adjustable tension mechanism that functions to adjust the tension force applied by the hoist to the garment.

In one embodiment, the system can include one or more motors that are connected to the adjustable tension mechanism of the one or more hoists. Each of the motors can be in communication with a controller having either a wired switch and/or a wireless remote control.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

As described herein, the term "removably secured" and derivatives thereof shall be used to describe a situation wherein two or more objects are joined together in a non-permanent manner so as to allow the same objects to be repeatedly joined and separated. This can be accomplished through the use of any number of commercially available connectors such as opposing strips of hook and loop material (i.e. Velcro®), magnetic elements, tethers such as straps and ties, and compression fittings such as hooks, snaps, buttons, clips and clamps such as carabiners, for example. Each illustrated connector can be permanently secured to the illustrated portion of the device via a permanent sealer such as glue, adhesive tape, or stitching, for example.

FIGS. 1-5B illustrate various embodiments of a personal radiation garment suspension system 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

Figure 1:
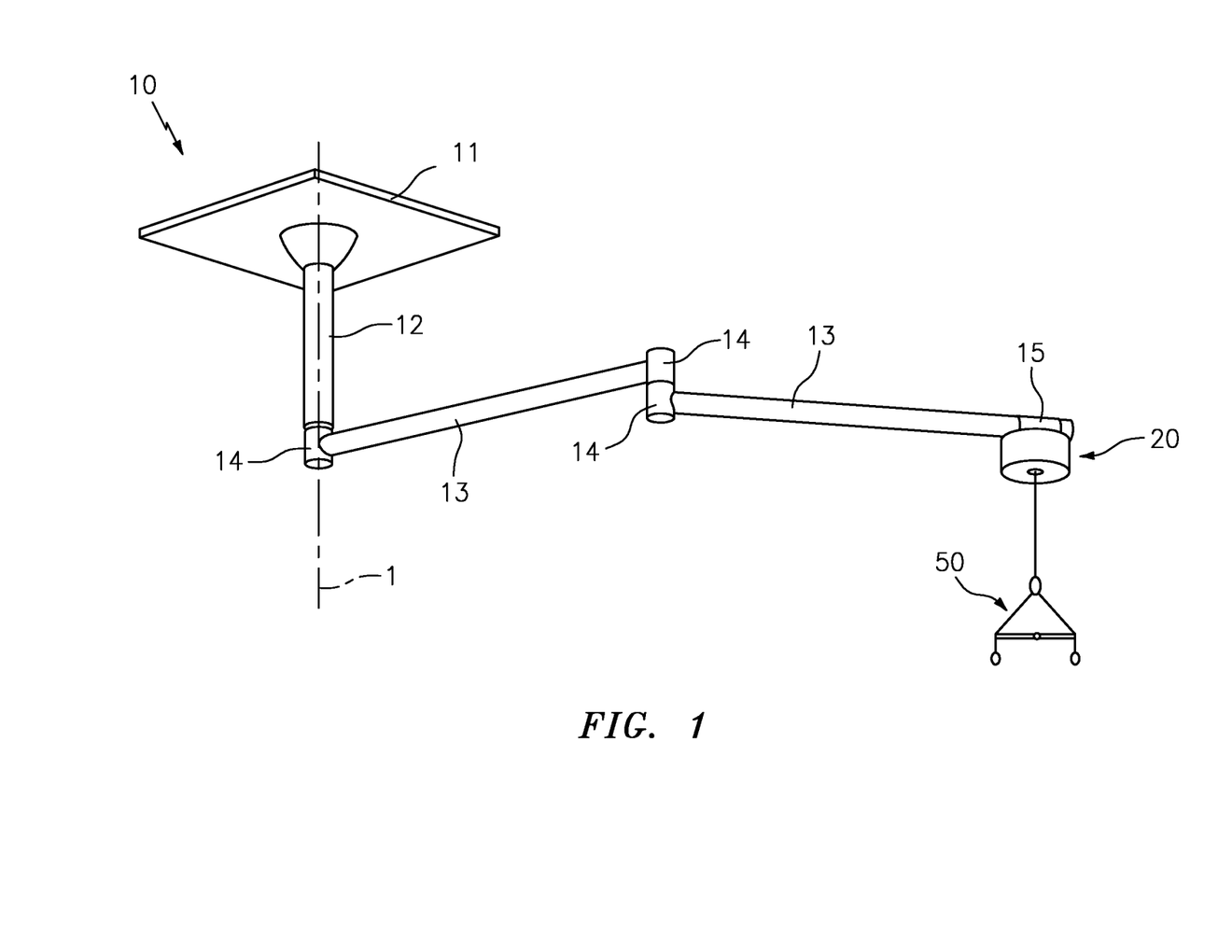
FIG. 1 is a perspective view of a personal radiation garment suspension system that is useful for understanding the inventive concepts disclosed herein.

As shown in FIG. 1, the system 10 can include a ceiling mount 11 having a flanged drop tube 12 extending vertically along axis 1, and one or more extension arms 13 that rotate horizontally via joints 14. A suspension assembly 20 can be positioned along the distal end of the outermost extension arm, and a garment coupler 50 can be suspended beneath the assembly to engage a personal radiation garment.

The ceiling mount 11 can include any number of devices capable of engaging a secondary structure, such as a ceiling joist or support beam, for example. The mount can include any number of different shapes, sizes, connection hardware (e.g., bolts and fasteners), and/or construction materials, and can function to securely position the system to an overhead environment.

The drop tube 12 can be connected to the ceiling mount and can extend downward therefrom. Depending on the size of the room in which the system 10 is to be installed, the drop tube 12 can include any number of different lengths and/or cross-sectional thicknesses for accommodating the forces applied to the system during use.

Each of the one or more extension arms 13 can be arranged at a perpendicular angle to the drop tube 12 and can extend outward therefrom in a horizontal orientation. As described herein, each of the extension arms can include any number of different lengths and/or cross-sectional thicknesses for accommodating the forces applied to the system during use. In this regard, the system can include a plurality of extension arms each having identical shapes and sizes, or can include a plurality of extension arms each having different shapes and/or sizes.

In one embodiment, one or more of the extension arms 13 can include, comprise or consist of two distinct segments that are slidingly engaged so as to be telescopic in nature. In either instance, the overall radial distance that can be covered by one or more extension arms can vary to suit the particular room in which the system is to be employed.

As described herein, both the drop tube 12 and the plurality of extension arms 13 may each be formed from materials that are, for example, relatively strong and stiff for their weight. Several nonlimiting examples include, but are not limited to various metals or metal alloys (e.g., aluminum, steel, titanium, or alloys thereof), plastic/polymers (e.g., high-density polyethylene (HDPE) or polyethylene terephthalate (PET)), and/or various composite materials (e.g., carbon fibers in a polymer matrix, etc.).

As shown, a plurality of joints 14 can be positioned between each of the extension arms 13 and the drop tube 12. Each of the joints can rotate the connected members 360 degrees along a single axis, so as to ensure the extension arms 13 do not tilt during device operation. Moreover, when connecting two extension arms together, two individual joints 14 can be stacked vertically. Such a feature provides a vertical offset that allows each distinct arm 13 to independently rotate 360 degrees about the joint and relative to each other.

Each of the joints can be constructed so as to rotate with absolute minimum resistance. Such a feature is important so as to not impede the movement of a system user, as will be described below. To this end, in the preferred embodiment each of the joints 14 can include, comprise or consist of tapered roller bearing-style joints that are known for superior performance with little to no noticeable resistance, and that support loading in both the radial and axial direction. One example of a suitable joint includes model 5709k88 tapered-roller bearings that are commercially available from McMaster-Carr®. Of course, any number of other devices are also contemplated.

Although not specifically illustrated, any number of different types of supporting hardware can be provided to ensure that each of the one or more extension arms remain at a completely horizontal orientation at all times. As such, in various embodiments, one or more diagonally oriented support brackets can extend from the drop tube 12 to the first extension arm 13. In such an embodiment, either the entire drop tube can rotate 360 degrees, and/or a secondary joint 14 can be provided at the connection point where the support bracket and the drop tube meet.

By providing a single fixed connection point to the building (e.g., the ceiling mount 11) and a plurality of arms that are independently manipulatable, the system advantageously eliminates the need for overhead channels, the ledges of which have a tendency to accumulate dust that is disturbed when a pulley rolls along the surface, thereby causing the dust to fall downward onto the system user and/or an otherwise sterile environment. Moreover, although a single extension arm is contemplated, the preferred embodiment will comprise two or more extension arms so as to reduce the amount of resistance to a user's movements caused by the device.

For example, if a 7 ft. radial coverage area is needed, utilizing a single 7 ft. extension arm would require moving the entire 7 ft. arm every time the user moved within the radial distance. However, by segmenting the extension arm into a plurality of distinct arms each rotatably connected to cover the desired radial area, motion of the system can be accomplished without moving all of the arms at once. Such a feature advantageously and inherently reduces the amount of resistance by a factor of the number of arms utilized.

FIGS. 2A-2D illustrate various embodiments of a suit suspension assembly 20, having a housing 21 that is connected 15 to the distal end of the outermost extension arm 13. The suspension assembly 20 can work in conjunction with the below described garment coupler 50 to provide a lifting/tension force onto any type of personal radiation garment. As will be described below, the lifting force can be adjustable so as to be less than, equal to, or slightly greater than the weight of the garment itself. Such a feature, in conjunction with the minimal resistance to movement described above functions to reduce the fatigue that is typically encountered by a user wearing heavy personal radiation garments for long periods of time.

The main body 21 can include a bottom wall, a top wall and a side wall of any number of different shapes and sizes forming a sealed housing for connecting and enclosing the below described components. In the preferred embodiment, the housing will be constructed from a durable, stiff material having excellent tensile strength such as metal, for example, so as to support the weight of the suit applied by the hoist.

The suspension connector 15 can connect the housing 21 to the distal end of one of the extension arms 13. As described herein, the connector can include any number or type of known fasteners such as a conduit strap, for example, and all associated mounting hardware (e.g., nuts, bolts) for securing the main body to the arm 13.

Figure 2A:
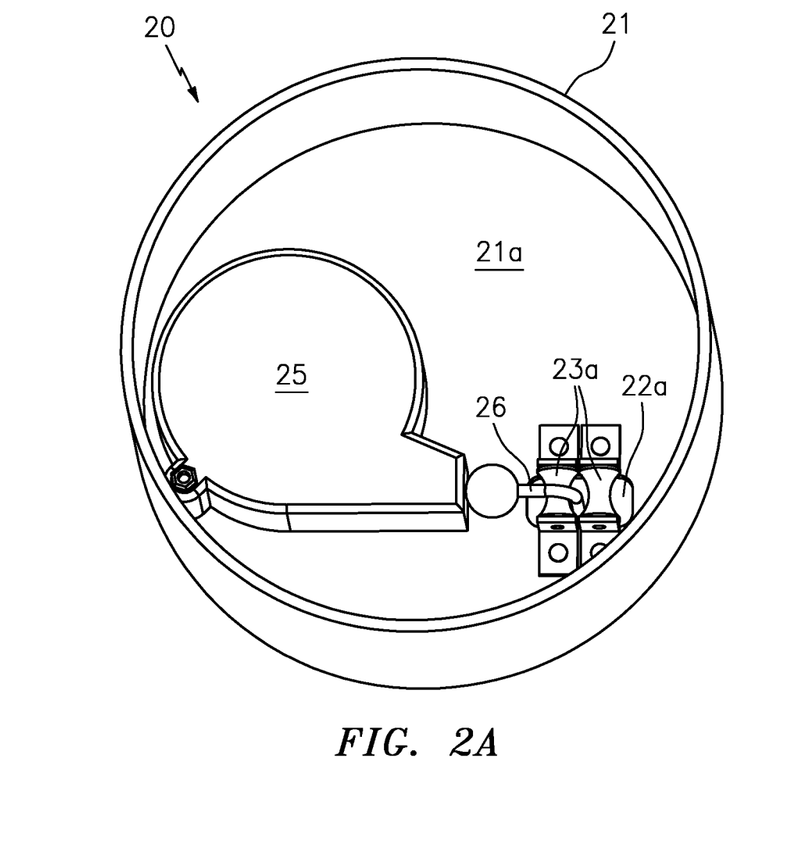
FIG. 2A is a top view of the suspension assembly with the top wall removed, in accordance with one embodiment of the invention.
Figure 2B:
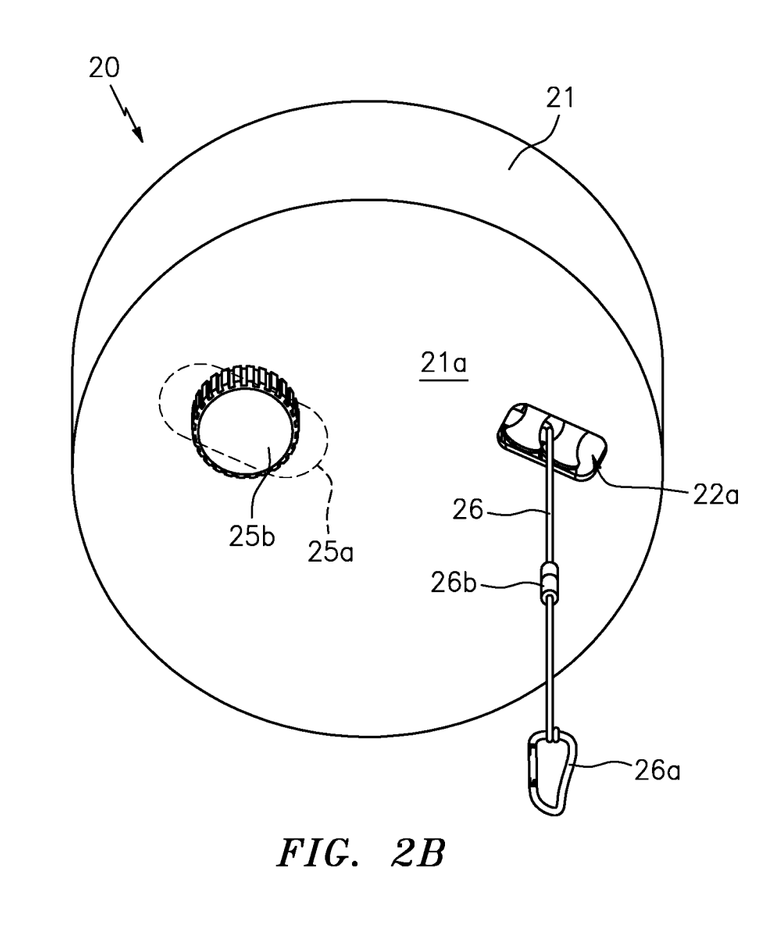
FIG. 2B is a bottom view of the suspension assembly shown in FIG. 2A.

As shown in FIGS. 2A and 2B, the suspension assembly 20 can include a first hoist 25 that can be positioned within the housing 21 and secured to the bottom wall 21a. The hoist can include an adjustable tensioning mechanism 25a having a manual actuator, such as a knob 25b, for example, to allow a user to manually adjust the tensioning force of the hoist cable 26. The cable extends from the hoist and can pass through an aperture 22a and a pair of cable reels 23a that are positioned along the bottom wall.

In the preferred embodiment, the hoist 25 can be positioned horizontally, with the cable 16 extending vertically. By positioning the major axis of the hoist horizontally, the same is able to fit within a housing having a minimum height (e.g., less than 5 inches). Such a feature advantageously provides a compact-height design that increases the ability of the system 10 to work in environments having low ceilings.

In one embodiment, one or more flaps made from a malleable material such as rubber, for example, can be positioned along the apertures of the main body and can be in communication with the cable(s). Such a feature advantageously functions to ensure any dust that has accumulated within the hoist(s) and that may be on the cable(s) remains within the sealed housing 21, thereby ensuring the dust or other such contaminants cannot fall downward onto a user and/or a sterile environment.

In the preferred embodiment, a carabiner 26a or other such connector can be disposed along the terminal end of the cable, and can function to engage the personal radiation coupler 50 and/or garment, as will be described below. Additionally, a quick release mechanism 26b, such as a shackle, pin or slip hook, for example, can be provided to ensure immediate separation of the system from the user in the event an excessive downward force is applied onto the system. Such a mechanism functions as a safety measure to prevent damage to the system in the event a user falls, for example.

As described herein, the hoist 25 can include, comprise or consist of any number of different devices capable of extending the cable, retracting the cable, applying a tensioning force onto the cable and/or supporting a hanging load. One suitable example of a hoist for use herein includes the model CP9922 tool balancer that is commercially available from Chicago Pneumatic®; however, other hoists are also contemplated.

Figure 2C:
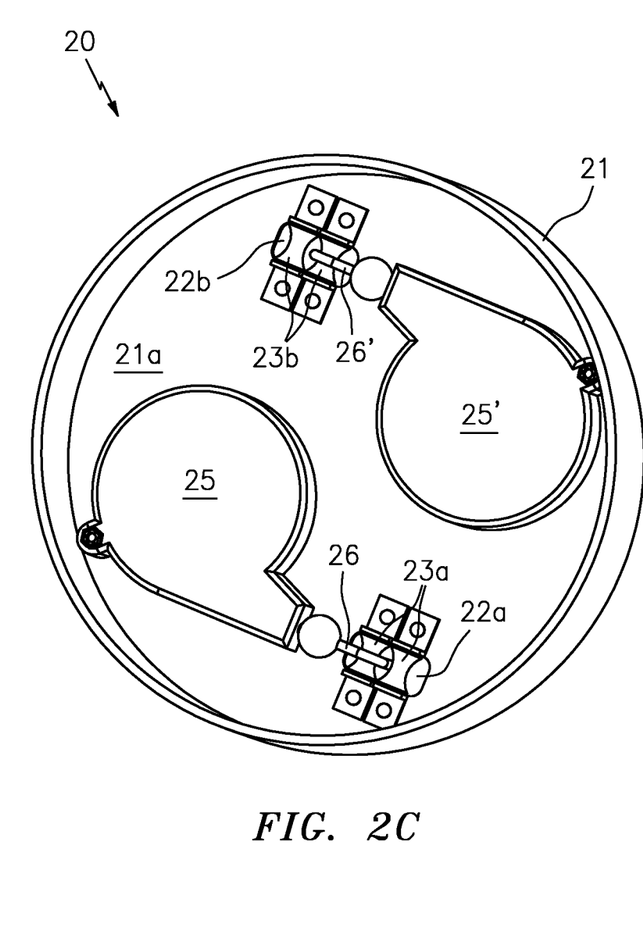
FIG. 2C is another top view of the suspension assembly with the top wall removed, in accordance with one embodiment of the invention.
Figure 2D:
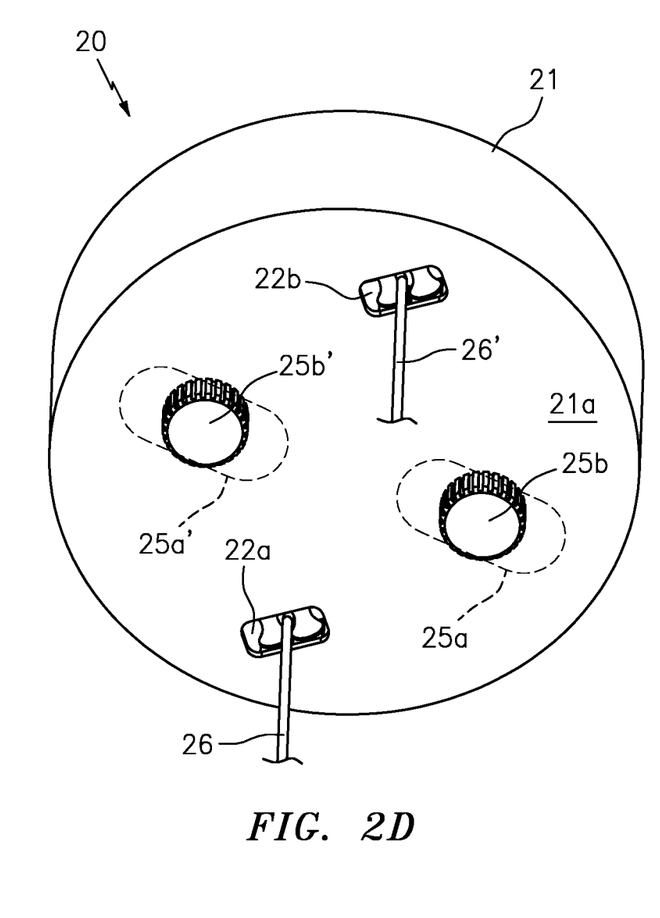
FIG. 2D is a bottom view of the suspension assembly shown in FIG. 2C.

Depending on the type or weight of the radiation garment to be connected to the system, more than one cable may be required for optimal performance. To this end, FIGS. 2C and 2D illustrate one embodiment of a suspension assembly 20 that includes a second hoist 25' that is also secured to the bottom wall 21a of the housing 21. Second hoist being identical to the first hoist, and also including an adjustable tensioner 25a' having a knob 25b' for allowing a user to manually adjust the lifting force of the second hoist cable 26'. The second cable extends from the hoist and passes through a second aperture 22b along the bottom wall, and can also include a pair of cable reels 23b.

Connectors 26a and 26a' can be positioned along the distal ends of the cables 26 and 26', respectively, and can engage the suit coupler 50 and/or the personal radiation garment 1, as will be described below.

Figure 3A:
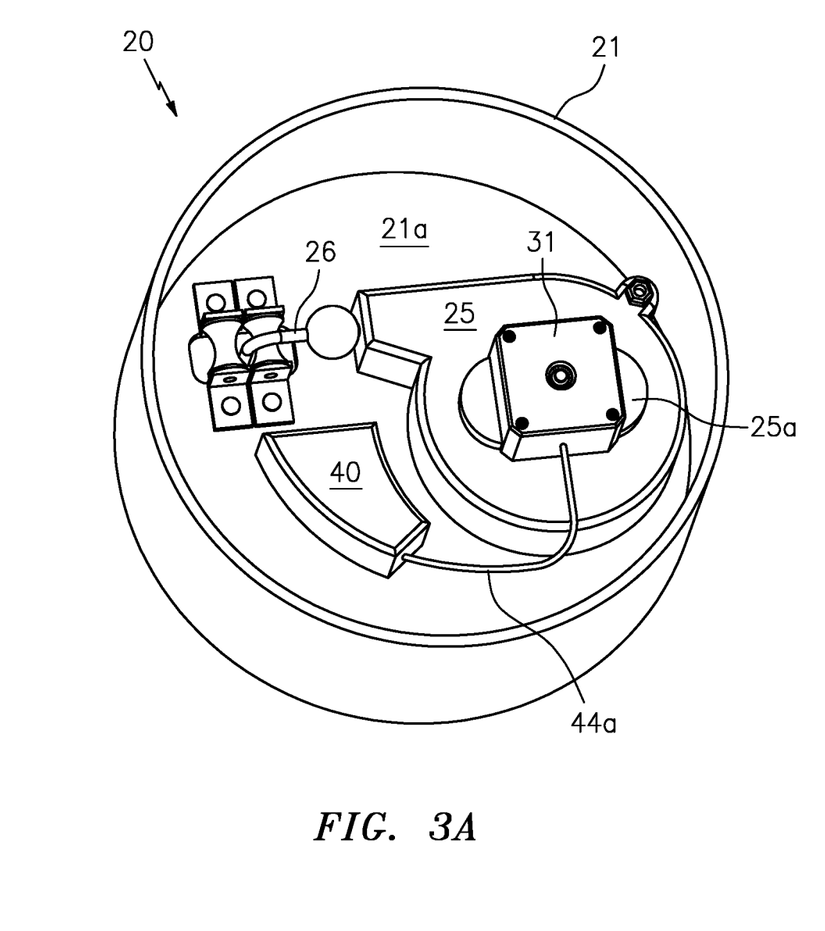
FIG. 3A is a top view of the suspension assembly with the top wall removed, in accordance with one embodiment of the invention.

Although described above as including a mechanical tensioning unit, other embodiments are also contemplated. To this end, FIG. 3A illustrates another embodiment of the suspension assembly 20 of FIGS. 2A and 2B that further includes a motor 31 that is in communication with the hoist 25, and a controller 40. In the illustrated embodiment, the hoist 25 can be positioned so that the adjustable tensioner 25a is located within the housing 21. When so positioned, the motor 31 can be connected to the tensioner so as to increase or decrease the tension force of the hoist depending on the rotation direction of the motor.

Figure 3B:
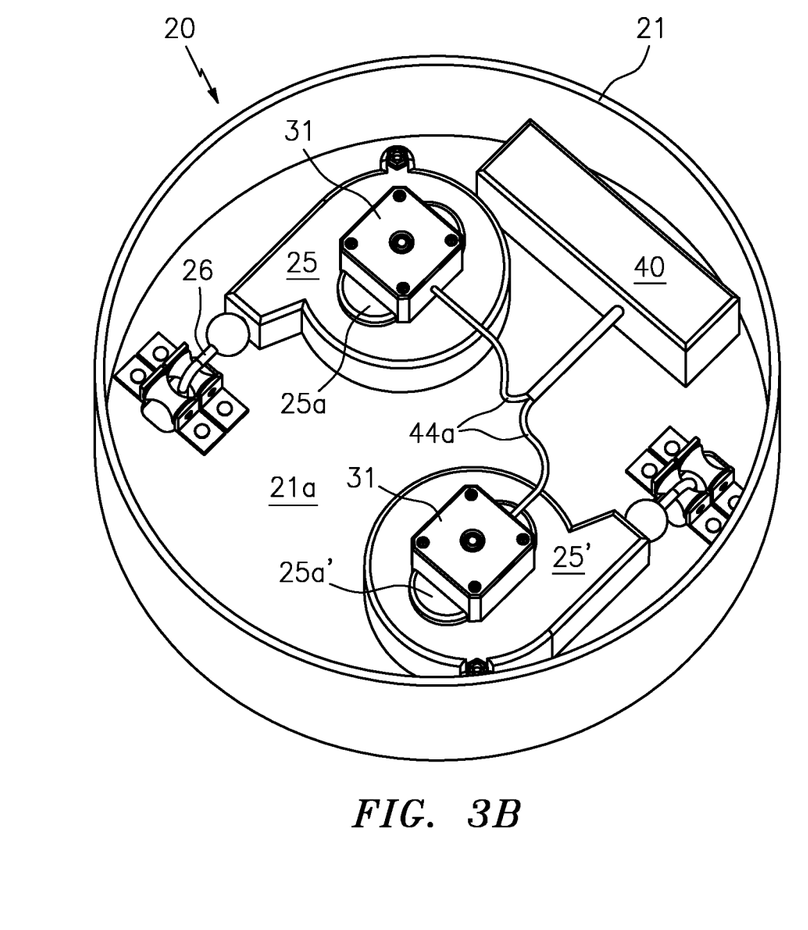
FIG. 3B is another top view of the suspension assembly with the top wall removed, in accordance with one embodiment of the invention.

Likewise, FIG. 3B illustrates another embodiment of the suspension assembly 20 of FIGS. 2C and 2D that further includes motors 31 and 31' that are in communication with hoists 25 and 25', respectively.

As described herein, motors 31 and 31' can each include, comprise or consist of any number of devices having a shaft that is capable of rotating in a controlled manner. In the preferred embodiment, the motor(s) can include a commercially available electrically powered stepper motor that moves in discrete steps, each comprising an incremental tensioning or de-tensioning of the cable. In such an embodiment, the stepper motor can be pre-calibrated to adjust the tensioning force by known amount (e.g., one pound-force, for example). Such a feature can work with the below described memory to allow users to quickly and easily set the system to apply a certain tension force depending on the type of garment and/or system user. Of course, other types of motors are also contemplated.

Figure 4:
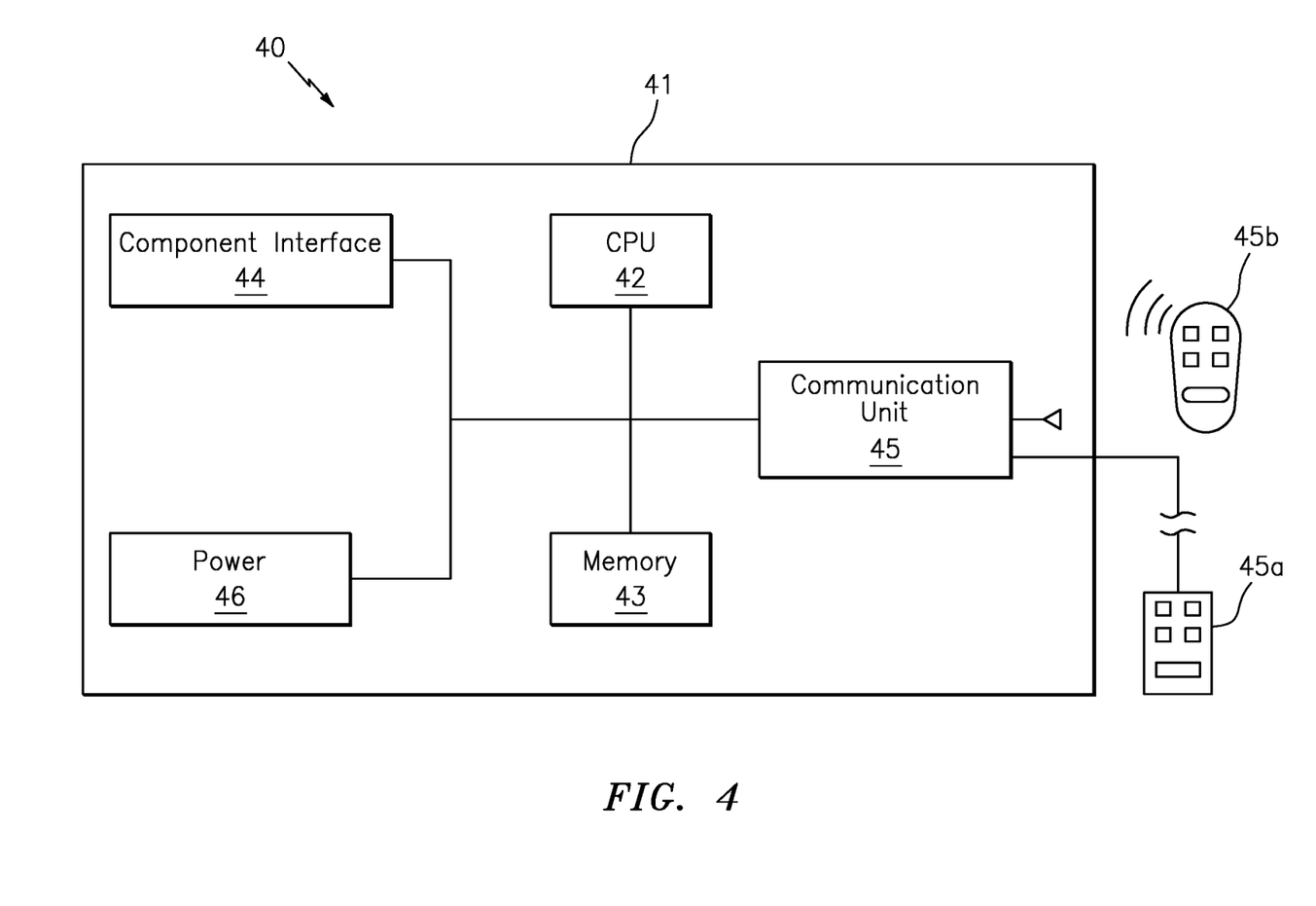
FIG. 4 is a simplified block diagram of the internal controller of the suspension system, in accordance with one embodiment of the invention.

The controller 40 can function to receive user inputs and control the operation of the motors 31 and 31'. As shown in FIG. 4, the controller can include an outer shell/body 41 for housing a processor 42 that is conventionally connected to an internal memory 43, a component interface unit 44, a communication unit 45, and/or a power source 46.

Although illustrated as separate elements, those of skill in the art will recognize that one or more system components may comprise, or include one or more printed circuit boards (PCB) containing any number of integrated circuit or circuits for completing the activities described herein. The CPU may be one or more integrated circuits having firmware for causing the circuitry to complete the activities described herein. Of course, any number of other analog and/or digital components capable of performing the below described functionality can be provided in place of, or in conjunction with the below described controller elements.

The main body 41 can include any number of different shapes and sizes, and can be constructed from any number of different materials suitable for encompassing each of the controller elements. In one preferred embodiment, the main body 41 can be constructed from lightweight injection molded plastic having a plurality of internal connectors (not shown) for securely housing each of the device elements. Of course, any number of other known construction materials such as PVC and composites, for example, are also contemplated.

The processor 42 can be a conventional central processing unit (CPU) or any other type of device, or multiple devices, capable of manipulating or processing information such as program code stored in the memory 43 in order to allow the device to perform the functionality described herein.

The memory 43 can act to store operating instructions in the form of program code for the processor 42 to execute. Although illustrated in FIG. 4 as a single component, memory 43 can include any number of physical memory devices such as, for example, local memory and/or one or more bulk storage devices. In one embodiment, the memory can store a plurality of preset configurations for instructing one or both of the motors to adjust the tension force of the one or more hoists. This can include adjusting each hoist to provide an identical tensioning force and/or adjusting each hoist to provide a different tensioning force. Such a feature being beneficial for users having uneven shoulders, for example. Such features are particularly beneficial for allowing the system to store and recall specific tensioning forces associated with particular users and/or types of garments having a known weight. Such memory features can be recalled and activated upon the user activating an appropriate control on the below described switch 45a and/or remote control 45b.

The component interface unit 44 can function to provide a communicative link between the processor 42 and various other components such as the communication unit 45 and the motor(s). In this regard, the component interface unit can include any number of different components such as one or more PIC microcontrollers, internal bus, cables 44a and other such hardware capable of providing a direct link between the various components. Of course, any other means for providing one or two-way communication between device components can also be utilized herein.

The communication unit 45 can include any number of components capable of sending and/or receiving signals with an externally located device, either directly or over a network. In one embodiment, the communication unit can include a wired connection to a switch 45a. Alternatively, or additionally, the communication unit can include a wireless transceiver for communicating wirelessly with an external device such as a smartphone, computer and/or remote control 45b, for example. In either instance, the communication unit can receive user instructions to selectively activate the motor(s) to adjust or set the tensioning force.

Any number of other known transmission and reception mechanisms and protocols can be utilized herein, several nonlimiting examples include Bluetooth, Near-Field-Communication (NFC) devices, unique radio frequencies, infrared signals (IR), and/or a network adapter functioning to communicate over a WAN, LAN or the internet via an internet service provider, for example.

The power source 46 can include any number of different components capable of providing the necessary power requirements to each element of the system. To this end, the power source can include or comprise a common A/C electrical power transformer and cord 46a capable of allowing the system to be powered from an electrical outlet. Additionally, the power source can include one or more batteries which can function to supply emergency power to the system components in the event of a power failure.

Although described above as including digital components, other embodiments of the controller are contemplated. For example, in an alternate embodiment the interface 44 can comprise an electrical relay that is physically connected to the switch 45a so as to selectively operate the motor(s) upon activation by a user.

Figure 5A:
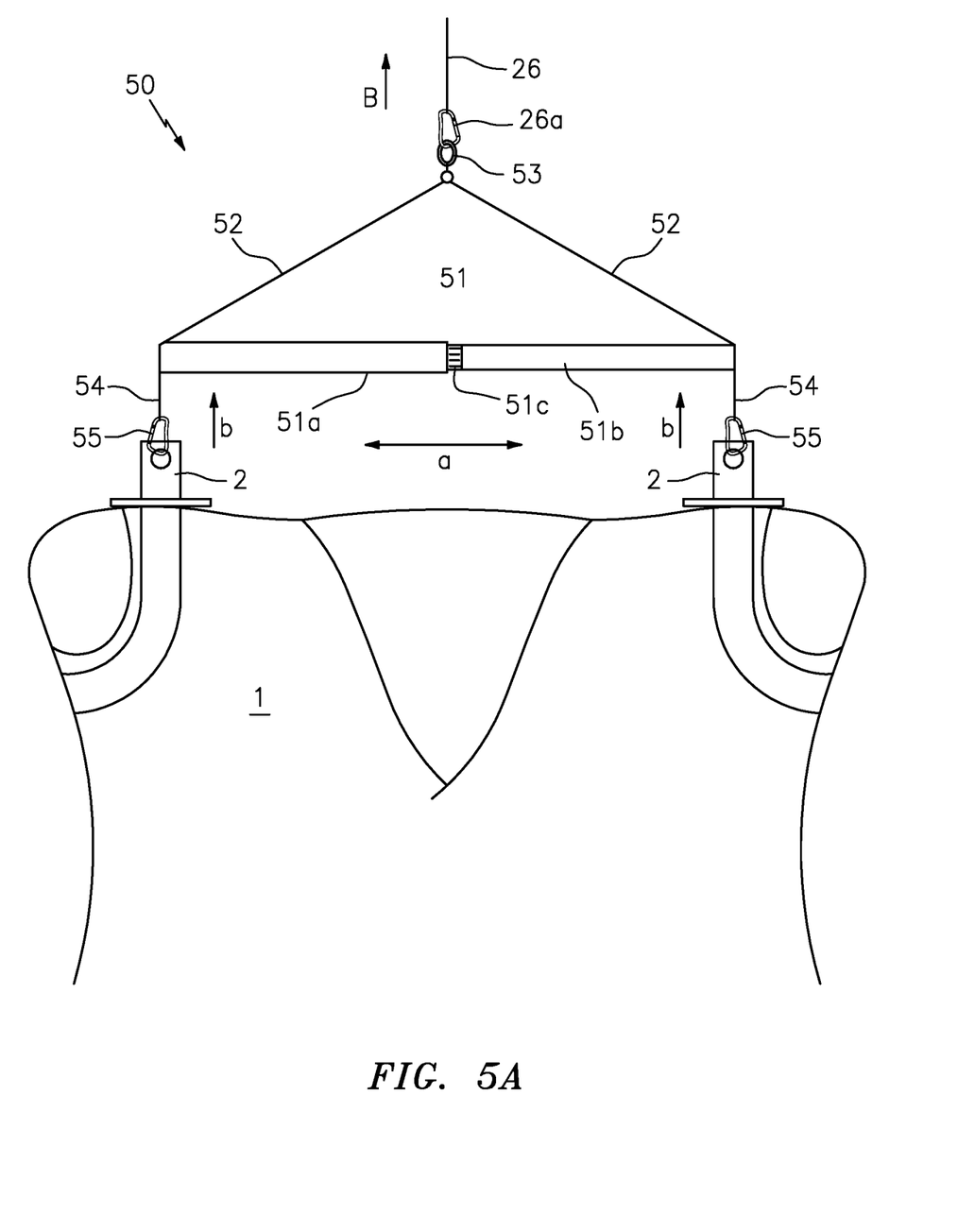
FIG. 5A is a perspective view of the suspension system in operation, in accordance with one embodiment of the invention.

FIG. 5A illustrates one embodiment of a suit coupler 50 that is configured to be suspended from a single cable emanating from the suspension assembly 20. As shown, the coupler can include an elongated shaft 51 having a pair of tethers 52 extending upward from each end. The tethers can be joined at their terminal ends by a connector 53, such as an oval screw lock, for example, that can also be engaged by the carabiner/hook 26a at the end of the cable 26. Likewise, a second pair of tethers 54 can extend downward from the distal ends of the shaft, and can each terminate into additional connectors 55, such as carabiners, for example.

In the preferred embodiment, the shaft 51 can comprise two distinct members 51a and 51b that are slidingly engaged so as to be telescopic in nature. Such a feature allows a user to adjust 51c the separation distance (see arrow a) between the tethers 55 to match the width of a user's shoulders. This advantageously ensures that the tensioning force applied by the suspension assembly 20 provides a purely vertical lifting force (arrow b) onto the garment, as opposed to an angular force.

Figure 5B:
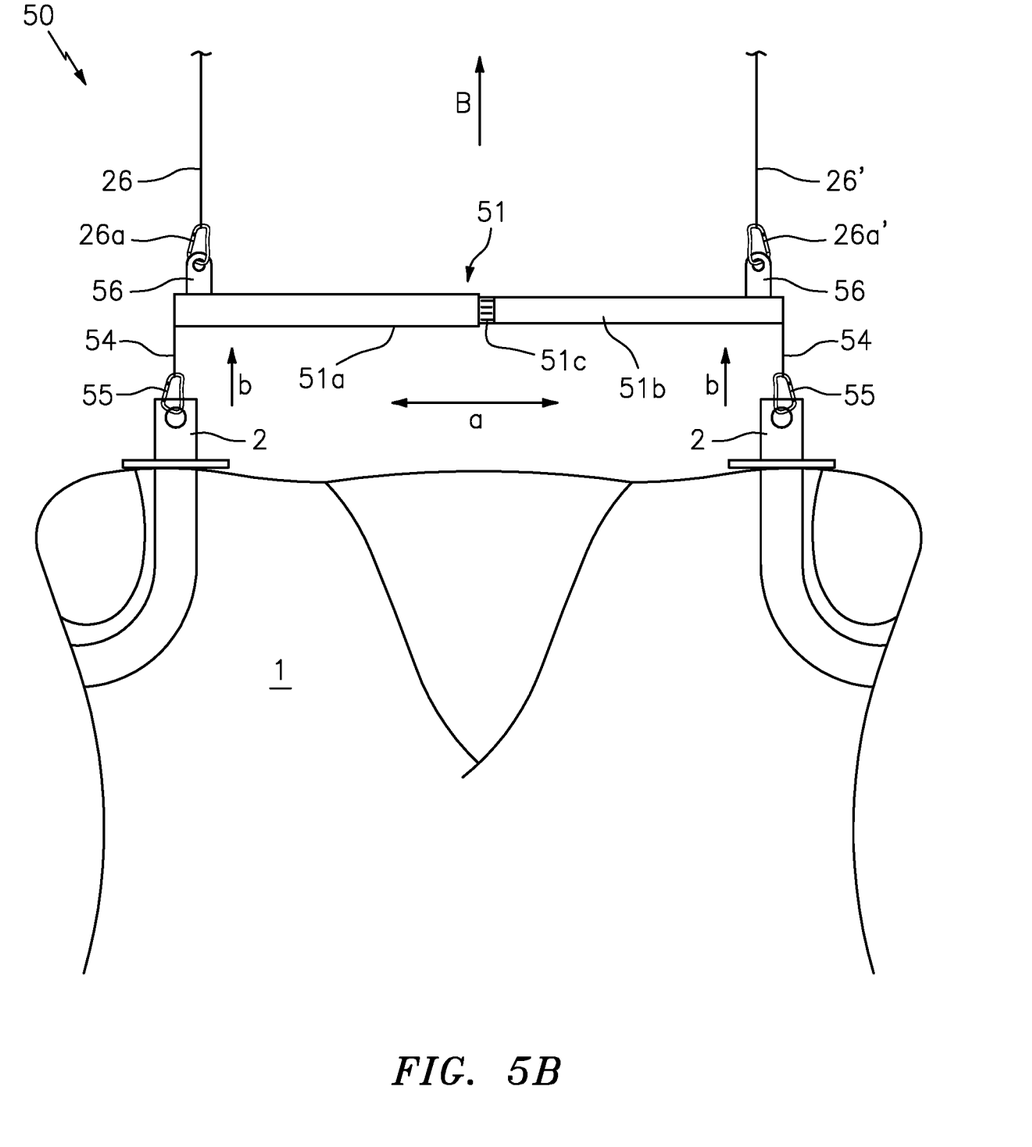
FIG. 5B is another perspective view of the suspension system in operation, in accordance with one embodiment of the invention.

Likewise, FIG. 5B illustrates one embodiment of a suit coupler 50 that is configured to be suspended from two cables emanating from the suspension assembly 20. As shown, the coupler can also include the elongated shaft 51, tethers 45 and connector 55. However, the dual tethers 52 can be replaced with rings 56 or other such connectors for engaging the pair of hooks 26a and 26a' at the ends of the cables 26 and 26', respectively.

In either instance, connectors 55 can each be connected directly to the radiation garment 1 and/or to suit hardware 2 such as hook apertures, for example that are positioned on a personal radiation garment 1. Such hardware can be permanently secured onto the garment or can be provided via a suspension adapter such as that described in U.S. Pat. No. 9,506,601, to Monir, the contents of which are incorporated herein by reference.

In operation, the cable(s) 26' and 26, and/or couplers 55 can be secured to the radiation garment 1 of a user as described above. Next, the tensioning mechanism of the hoist(s) can be adjusted to impart a lifting force (i.e., tensioning force) B onto the suit. The tensioning force will preferably be equal to the total weight of the suit, so that the user is no longer able to feel the weight of the suit on their shoulders. As noted above, the tensioning force can be adjusted manually and/or automatically using a switch or remote control.

Finally, once the tension force has been adjusted, the user can move freely around the radial distance extending outward from the ceiling mount 11. When doing so, the low resistance offered by the combination of the extension arms 13 and joints 14 ensures the user will not need to pull or otherwise guide the overhead system. Stated differently, the system is designed to ensure the users natural movements are sufficient to orient the outermost arm 13 at a location that positions and maintains the suspension assembly 20 above the user's head at all times, thereby imparting a purely vertical lifting/tension force onto the garment 1.

Because the system imparts a constant user-defined tensioning force, the vertical movement of the cable will move in accordance with a user's movements. For example, when the user leans or bends downward, the hoist(s) will continue to impart the same constant tensioning force as the cable extends and retracts within the hoist in harmony with the user'-s movements. Stated differently, the system will impart the same tensioning force onto a user when that user is in a standing position, leaning or bent position.

As described herein, one or more elements of the personal radiation garment suspension system 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the terms "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A suspension system for a personal radiation garment, said suspension system comprising:
    a ceiling mount;
    a drop tube having a first end that is in communication with the ceiling mount;
    at least one extension arm that is in a perpendicular orientation to the drop tube;
    a joint that is interposed between a second end of the drop tube and a first end of the at least one extension arm, said joint including a rotary bearing to rotate each of the at least one extension arm 360 degrees axially;
    a suspension assembly that is fixedly disposed along a distal end of the at least one extension arm, said assembly including at least one hoist having a first cable; and
    a suit coupler that is in communication with each of the at least one cable, said coupler being configured to engage a personal radiation garment
    wherein the suspension assembly includes a housing having an interior space, and
    wherein each of the at least one hoist is positioned within the interior space.

2. The system of claim 1, wherein the suit coupler includes an elongated shaft having a first pair of tethers extending upward at a diagonal angle, said first pair of tethers being removably secured to a distal end of the first cable; and
    a second pair of tethers extending downward at a parallel orientation to each other, said second pair of tethers including couplers for removably engaging the personal radiation garment.

3. The system of claim 2, wherein the elongated shaft includes an adjustable length.

4. The system of claim 1, wherein the at least one extension arm comprises a plurality of extension arms; and
    each of the plurality of extension arms are connected by additional joints and are configured to independently rotate 360 degrees axially.

5. The system of claim 1, wherein the housing includes a bottom wall, a side wall, and a top wall that define an interior space; and
    an aperture that is disposed along the bottom wall.

6. The system of claim 5, wherein the first cable extends through the aperture.

7. The system of claim 1, wherein the at least one hoist includes an adjustable tensioner.

8. The system of claim 7, further comprising:
    a motor that is connected to the adjustable tensioner.

9. The system of claim 8, wherein the motor comprises a stepper motor.

10. The system of claim 8, further comprising:
    a controller that is in communication with the motor.

11. The system of claim 10, further comprising:
    a switch that is in communication with the controller, said switch being configured to instruct the controller to selectively activate the motor.

12. The system of claim 11, wherein the switch is hard wired to the controller.

13. The system of claim 11, wherein the switch is in wireless communication with the controller.

14. The system of claim 1, further comprising:
    at least one opening that is positioned along a bottom end of the housing at a location adjacent to each of the at least one hoist, each of the at least one opening including a size that is suitable for receiving a cable that is attached to one of the at least one hoist.

15. The system of claim 14, further comprising:
    a plurality of malleable dust flaps that are positioned adjacent to each of the at least one opening, said flaps functioning to prevent dust from exiting the interior space of the housing.

* * * * *